United States Patent
Tsapakh et al.

(10) Patent No.: US 7,156,968 B2
(45) Date of Patent: Jan. 2, 2007

(54) ELECTRODE COMPRISING MATERIAL TO HELP STABILIZE OXIDE OF CATALYST FOR ELECTROCHEMICAL SENSOR

(75) Inventors: Serguei Tsapakh, Saint-Petersburg (RU); Kathrin Keller, Königswinter (DE); Andreas Röhrl, Köln (DE)

(73) Assignee: MST Technology GmbH, Hohenschaftlarn (DE)

( * ) Notice: Subject to any disclaimer, the term of this patent is extended or adjusted under 35 U.S.C. 154(b) by 68 days.

(21) Appl. No.: 10/435,618

(22) Filed: May 9, 2003

(65) Prior Publication Data

US 2004/0222093 A1    Nov. 11, 2004

(51) Int. Cl.
*G01N 27/404* (2006.01)
*G01N 27/30* (2006.01)

(52) U.S. Cl. .................. 204/431; 204/292; 205/782
(58) Field of Classification Search ............... 204/400, 204/412, 431, 432, 280, 292; 205/782, 782.5, 205/783, 794.5
See application file for complete search history.

(56) References Cited

U.S. PATENT DOCUMENTS

| | | | | |
|---|---|---|---|---|
| 3,768,259 A | * | 10/1973 | Carnahan et al. | 60/276 |
| 3,775,183 A | * | 11/1973 | Paulson | 429/144 |
| 4,642,172 A | | 2/1987 | Fruhwald | |
| 5,037,525 A | * | 8/1991 | Badwal | 204/421 |
| 5,162,169 A | * | 11/1992 | Tomantschger et al. | 429/59 |
| 5,344,546 A | * | 9/1994 | Kiesele et al. | 204/415 |
| 5,635,627 A | | 6/1997 | Bytyn | |
| 6,337,006 B1 | * | 1/2002 | Fujita et al. | 204/421 |
| 6,423,209 B1 | * | 7/2002 | Weber et al. | 205/775 |
| 2002/0027086 A1 | | 3/2002 | Saffell et al. | |

FOREIGN PATENT DOCUMENTS

EP    0 387 044    * 9/1990

OTHER PUBLICATIONS

Bard and Faulkner, Electrochemical Methods, Fundamentals and Applications, 2001, pp. 24-28.*
Merck Index, 12th Ed, 1996, entry No. 537.*

* cited by examiner

*Primary Examiner*—Kaj K. Olsen
(74) *Attorney, Agent, or Firm*—Steven J. Hultquist; Intellectual Property Technology Law (57) ABSTRACT

An electrode comprises a catalyst and material to help stabilize an oxide of the catalyst. The electrode for one embodiment may be used for an electrochemical sensor or sensor cell.

28 Claims, 2 Drawing Sheets

ELECTRODE COMPRISING MATERIAL TO HELP STABILIZE OXIDE OF CATALYST FOR ELECTROCHEMICAL SENSOR

TECHNICAL FIELD

One or more embodiments described in this patent application relate to the field of electrochemical sensors.

BACKGROUND ART

Electrochemical sensors may be used for a wide variety of purposes. Carbon monoxide (CO) sensors, for example, may be used to help detect unsafe levels of carbon monoxide (CO) in a home or garage, for example. Carbon monoxide (CO) sensors may also be used for flue gas analysis in an environment where both carbon monoxide (CO) and hydrogen ($H_2$) may be present. Carbon monoxide (CO) sensors that use a measuring electrode of platinum black (Pt), however, also respond to hydrogen ($H_2$) and therefore may falsely identify the presence of carbon monoxide (CO).

SUMMARY

One or more embodiments of an electrode comprise a catalyst and material to help stabilize an oxide of the catalyst.

One or more embodiments of a sensor cell comprise an electrolyte and an electrode comprising a catalyst and material to help stabilize an oxide of the catalyst.

One or more embodiments of an electrochemical sensor comprise a measuring electrode comprising a catalyst and material to help stabilize an oxide of the catalyst, a counter electrode, an electrolyte, and sensor operating circuitry coupled to the measuring electrode and counter electrode.

One or more embodiments of a method comprise forming two or more electrodes and positioning the two or more electrodes relative to a reservoir to couple the two or more electrodes to an electrolyte in the reservoir. At least one electrode comprises a catalyst and material to help stabilize an oxide of the catalyst.

One or more embodiments of another method comprise biasing one or more electrodes coupled to an electrolyte, measuring any current produced from one of the electrodes, and identifying whether a target particle is present based on the measured current. At least one electrode comprises a catalyst and material to help stabilize an oxide of the catalyst.

BRIEF DESCRIPTION OF THE DRAWINGS

One or more embodiments are illustrated by way of example and not limitation in the figures of the accompanying drawings, in which like references indicate similar elements and in which.

DETAILED DESCRIPTION

The following detailed description sets forth an embodiment or embodiments for an electrode comprising material to help stabilize an oxide of a catalyst for an electrochemical sensor.

Sensor

Figure 1:
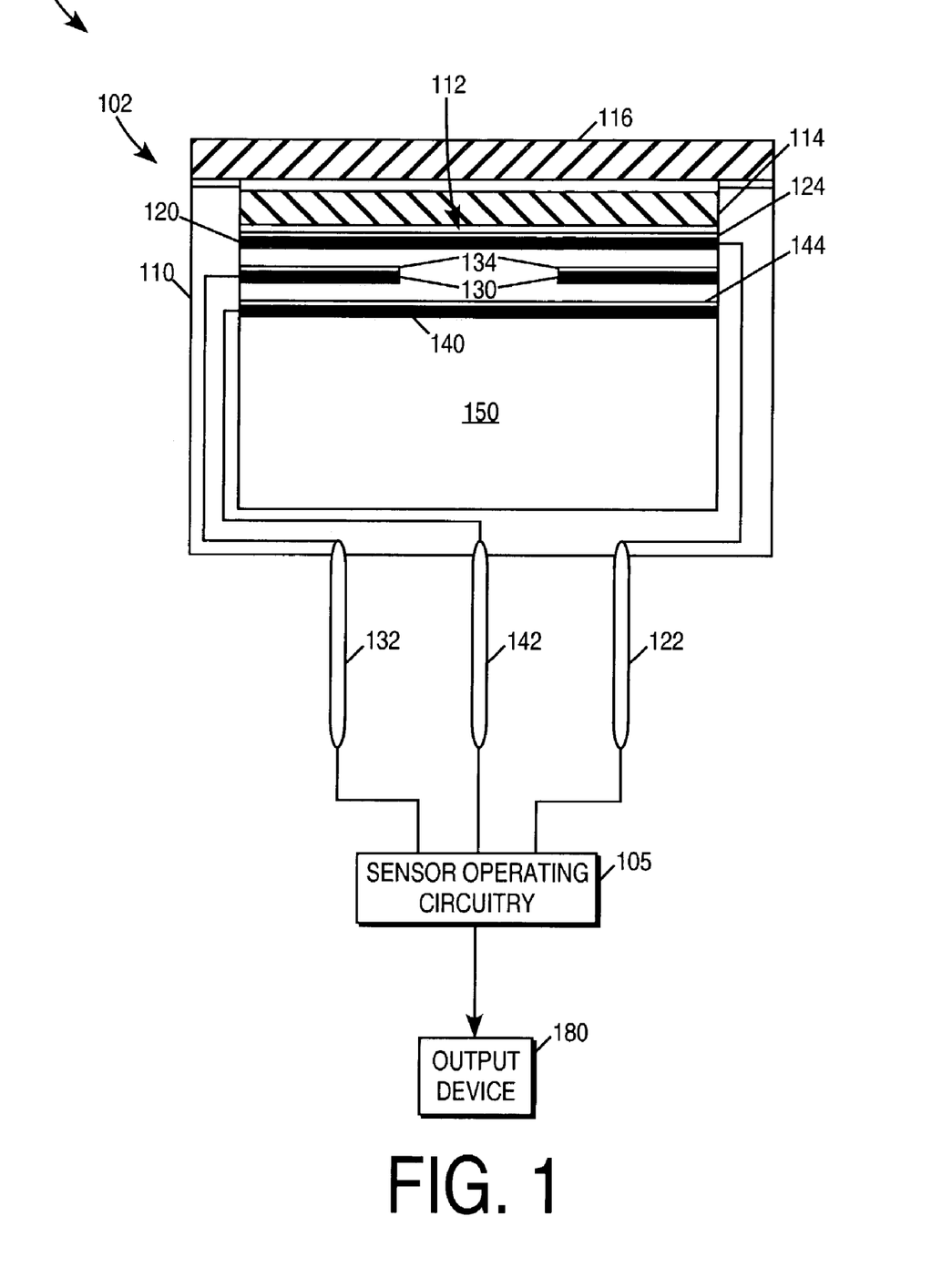
FIG. 1 illustrates, for one embodiment, an electrochemical sensor having an electrode comprising a catalyst and material to help stabilize an oxide of the catalyst.

FIG. 1 illustrates, for one embodiment, an electrochemical sensor 100. Sensor 100 may be used to sense any suitable target particle in any suitable environment for any suitable purpose.

Sensor 100 for one embodiment comprises a measuring electrode 120 comprising a catalyst to sense one or more suitable target particles, such as carbon monoxide (CO) for example. Measuring electrode 120 for one embodiment also comprises material to help stabilize an oxide of the catalyst. The material for one embodiment may help stabilize an oxide of the catalyst formed on a surface of measuring electrode 120. Stabilizing an oxide of the catalyst for one embodiment helps reduce or minimize sensitivity of measuring electrode 120 to a potentially interfering non-target particle, such as hydrogen ($H_2$) for example, that measuring electrode 120 may otherwise sense as a target particle. Measuring electrode 120 for one embodiment comprises a catalyst comprising platinum (Pt) to sense carbon monoxide (CO), for example, and comprises a suitable metal oxide to help stabilize a platinum oxide ($Pt_xO_y$) in measuring electrode 120 to help reduce or minimize the cross-sensitivity of measuring electrode 120 to hydrogen ($H_2$).

As illustrated in FIG. 1, sensor 100 for one embodiment comprises a sensor cell 102 and sensor operating circuitry 105 conductively coupled to sensor cell 102. Sensor operating circuitry 105 for one embodiment may also be coupled to or in wireless communication with an output device 180. Output device 180 may be local to or remote from sensor operating circuitry 105 and may or may not be a component of sensor 100.

Sensor cell 102 for one embodiment comprises a housing 110, measuring electrode 120, a reference electrode 130, a counter electrode 140, an electrolyte 150, and electrical contacts 122, 132, and 142. Although described as having three electrodes, sensor cell 102 for another embodiment may have only two electrodes or may have more than three electrodes. Sensor cell 102 for another embodiment may not have reference electrode 130, for example.

Housing 110 for one embodiment defines an electrolyte reservoir of any suitable size and shape to hold electrolyte 150 and is configured to help support measuring electrode 120, reference electrode 130, and counter electrode 140 such that at least a portion of each of measuring electrode 120, reference electrode 130, and counter electrode 140 are coupled to electrolyte 150. Housing 110 for one embodiment may help support measuring electrode 120 in any suitable position in the electrolyte reservoir such that at least a portion of measuring electrode 120 is immersed in electrolyte 150. Housing 110 for one embodiment may help support both reference electrode 130 and counter electrode 140 in any suitable position in the electrolyte reservoir such that both reference electrode 130 and counter electrode 140 are immersed in electrolyte 150.

Measuring electrode 120, reference electrode 130, and counter electrode 140 for one embodiment may each have any suitable size and shape for positioning in the electrolyte reservoir. Where the electrolyte reservoir is shaped as a hollowed cylinder, for example, measuring electrode 120 for one embodiment may be disc-shaped and reference electrode 130 and counter electrode 140 for one embodiment may be ring-shaped or disc-shaped.

Housing 110 for one embodiment defines an opening 112 of any suitable size and shape through which a target particle may pass from an environment external to housing 110 to measuring electrode 120. Housing 110 may define opening 112 and help support measuring electrode 120 in any suitable position relative to one another. For one embodiment, housing 110 may help support a membrane 124 in any suitable position relative to opening 112 and to measuring electrode 120 to allow a target particle to diffuse through membrane 124 to measuring electrode 120 and to help prevent electrolyte 150 from passing through membrane 124 and out of the electrolyte reservoir. Membrane 124 for one embodiment, as illustrated in FIG. 1, may be coupled to measuring electrode 120. Membrane 124 may be formed from any suitable material, such as polytetrafluoroethylene (PTFE) for example.

Housing 110 for one embodiment may also help support an optional chemical filter 114 in any suitable position relative to opening 112 to help prevent one or more poisons that may damage measuring electrode 120 and/or one or more potentially interfering non-target particles that may otherwise be sensed by measuring electrode 120 as target particles from reaching measuring electrode 120. Housing 110 for one embodiment may also help support an optional dust filter 116 in any suitable position relative to opening 112 to help prevent dust, dirt, mites, etc. from interfering with sensor cell 102.

Housing 110 for one embodiment may define an optional opening of any suitable size and shape through which oxygen ($O_2$), for example, may pass from an environment external to housing 110 to counter electrode 140. Housing 110 may define such an opening and help support counter electrode 140 in any suitable position relative to one another. For one embodiment, housing 110 may help support a suitable membrane in any suitable position relative to such an opening and to counter electrode 140 to allow oxygen ($O_2$), for example, to diffuse through such a membrane to counter electrode 140 and to help prevent electrolyte 150 from passing out of the electrolyte reservoir.

Housing 110 for another embodiment may be configured to help support measuring electrode 120, reference electrode 130, and counter electrode 140 for coupling to electrolyte 150 in any other suitable manner. Housing 110 for one embodiment may be configured to help support measuring electrode 120, reference electrode 130, and/or counter electrode 140 external to an electrolyte reservoir for coupling to an electrolyte through wetting filters, for example, coupled to porous walls, for example, helping to define the reservoir.

Housing 110 for one embodiment helps support electrical contacts 122, 132, and 142. Electrical contacts 122, 132, and 142 are conductively coupled to measuring electrode 120, reference electrode 130, and counter electrode 140, respectively. Electrical contacts 122, 132, and 142 are to be conductively coupled to sensor operating circuitry 105 to conductively couple measuring electrode 120, reference electrode 130, and counter electrode 140, respectively, to sensor operating circuitry 105. Electrical contacts 122, 132, and 142 for one embodiment, as illustrated in FIG. 1, may be shaped as pins for insertion into corresponding socket openings of a connector for sensor operating circuitry 105. Electrical contacts 122, 132, and 142 for another embodiment may be shaped in any other suitable manner.

For another embodiment, sensor operating circuitry 105 may be directly coupled to measuring electrode 120, reference electrode 130, and counter electrode 140.

Housing 110 may be formed from any suitable material. Housing 110 for one embodiment may be formed from a suitable material that resists corrosion.

Sensor operating circuitry 105 is to operate sensor 100 to sense one or more target particles in an environment near sensor cell 102. Sensor operating circuitry 105 may be conductively coupled to sensor cell 102 either locally in or near the same environment or remotely.

Sensor Use

Figure 2:
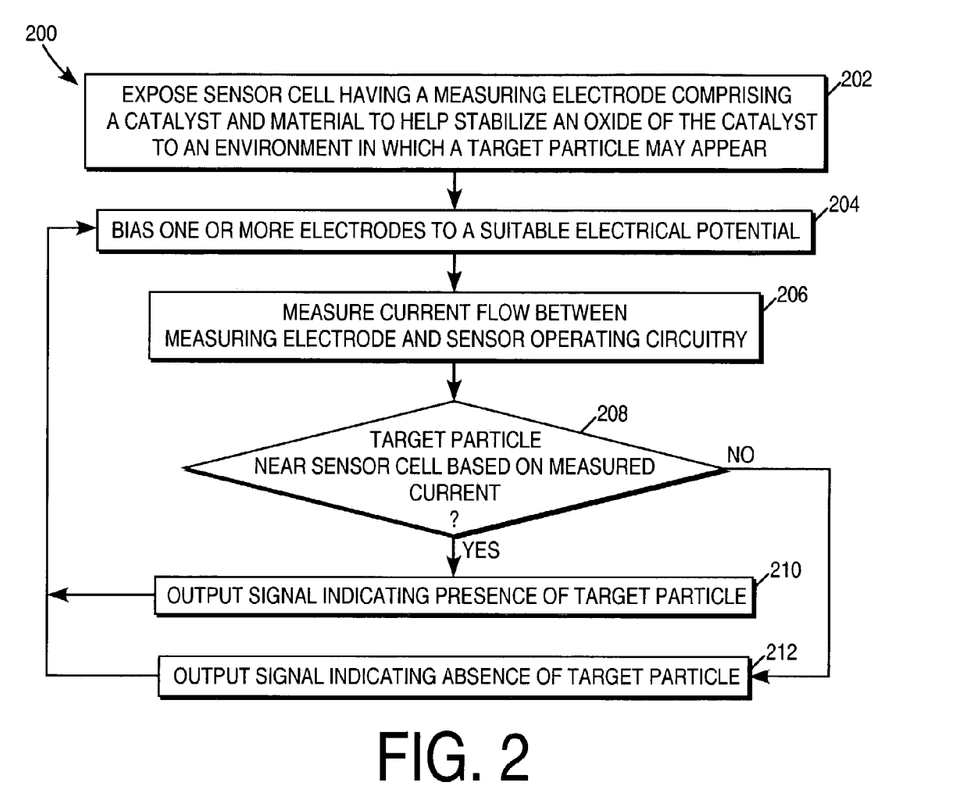
FIG. 2 illustrates, for one embodiment, a flow diagram to use an electrochemical sensor having an electrode comprising a catalyst and material to help stabilize an oxide of the catalyst.

FIG. 2 illustrates, for one embodiment, a flow diagram 200 to use sensor 100.

For block 202 of FIG. 2, sensor cell 102 is exposed to an environment in which a target particle may appear. Sensor cell 102 may be exposed to any suitable environment in which any suitable one or more target particles may appear. The target particle(s) to be sensed may depend, for example, on the material used for measuring electrode 120 and counter electrode 140 and on the circuitry used for sensor operating circuitry 105. Sensor cell 102 for one embodiment may be exposed to an environment in which carbon monoxide (CO) may appear. Sensor cell 102 for one embodiment may be exposed to an environment in which carbon monoxide (CO) appears in the presence of hydrogen ($H_2$).

For blocks 204, 206, 208, 210, and 212, sensor operating circuitry 105 operates sensor 100 to sense one or more target particles.

For block 204, sensor operating circuitry 105 biases one or more electrodes to a suitable electrical potential. Sensor operating circuitry 105 for one embodiment may comprise any suitable circuitry to bias measuring electrode 120, reference electrode 130, and/or counter electrode 140 in any suitable manner relative to one another and/or relative to ground.

Reference electrode 130 for one embodiment helps provide a relatively stable electrochemical potential as reference for sensor operating circuitry 105. Sensor operating circuitry 105 for one embodiment helps hold the electrochemical potential of reference electrode 130 relatively constant such that approximately no electrical current flows through reference electrode 130 to provide what is known as a quasi-reference electrode. For another embodiment, reference electrode 130 may be what is known as a true reference electrode by using, for example, Ag/AgCl, a standard calomel electrode, or $Hg/Hg_2SO_4$ for reference electrode 130.

Sensor operating circuitry 105 for one embodiment may help bias measuring electrode 120 relative to reference electrode 130 at a relatively constant electrical potential. Sensor operating circuitry 105 for another embodiment may help maintain both measuring electrode 120 and reference electrode 130 generally at the same electrical potential. Sensor operating circuitry 105 for one embodiment may allow the electrical potential at counter electrode 140 to vary.

Measuring electrode 120 comprises a catalyst to help precipitate a reaction of target particles that pass through opening 112 and membrane 124 of sensor cell 102 and contact measuring electrode 120. Measuring electrode 120 for one embodiment may catalyze the oxidation of a target particle to produce the oxidized target particle, ions ($H^+$), and electrons ($e^-$). Measuring electrode 120 may also be called a working electrode or a sensing electrode.

For one embodiment where a target particle is carbon monoxide (CO), measuring electrode 120 catalyzes the oxidation of carbon monoxide (CO) to carbon dioxide ($CO_2$) as follows.

$$CO + H_2O \rightarrow CO_2 + 2H^+ + 2e^-$$

The resulting ions ($H^+$) flow through electrolyte 150 to counter electrode 140 while the resulting electrons ($e^-$) flow to sensor operating circuitry 105, allowing sensor operating circuitry 105 to identify a presence of carbon monoxide (CO) in an environment near sensor cell 102. The resulting carbon dioxide ($CO_2$) passes back through membrane 124, for example, into an environment external to sensor cell 102.

Counter electrode 140 comprises a catalyst for a corresponding but converse counter reaction at counter electrode 140. Counter electrode 140 for one embodiment may catalyze the reduction of oxygen ($O_2$) to produce water ($H_2O$).

For one embodiment where measuring electrode 120 catalyzes the oxidation of carbon monoxide (CO), counter electrode 140 catalyzes the reduction of oxygen ($O_2$) as follows:

$$O_2 + 4H^+ + 4e^- \rightarrow 2H_2O$$

and therefore helps avoid consumption of components of sensor cell 102 in completing the overall sensor cell reaction as follows.

$$2CO + O_2 \rightarrow 2CO_2$$

Counter electrode 140 for one embodiment may receive oxygen ($O_2$) saturated in electrolyte 150 and/or through an optional opening in the electrolyte reservoir near counter electrode 140. Counter electrode 140 for one embodiment may receive ions ($H^+$) flowing through electrolyte 150 from measuring electrode 120 and may receive electrons ($e^-$) from sensor operating circuitry 105.

The catalyst of measuring electrode 120 for one embodiment may also help precipitate a reaction of potentially interfering non-target particles that appear in an environment near sensor cell 102 and that pass through opening 112 and membrane 124 of sensor cell 102 and contact measuring electrode 120.

As one example, the catalyst of measuring electrode 120 may catalyze the oxidation of hydrogen ($H_2$) as follows:

$$H_2 \rightarrow 2H^+ + 2e^-$$

while counter electrode 140 catalyzes the reduction of oxygen ($O_2$) as follows:

$$O_2 + 4H^+ + 4e^- \rightarrow 2H_2O$$

to complete the overall sensor cell reaction as follows.

$$2H_2 + O_2 \rightarrow 2H_2O$$

Because the reaction of potentially interfering non-target particles at measuring electrode 120 may induce a current between measuring electrode 120 and sensor operating circuitry 105, sensor operating circuitry 105 could falsely identify a presence of a target particle in an environment near sensor cell 102.

To help reduce or minimize this cross-sensitivity to a non-target particle, measuring electrode 120 for one embodiment comprises material to help stabilize an oxide of the catalyst in measuring electrode 120. The material for one embodiment may help stabilize an oxide of the catalyst formed on a surface of measuring electrode 120. Measuring electrode 120 for one embodiment may comprise material that helps form an oxide of the catalyst in measuring electrode 120.

For one embodiment where measuring electrode 120 comprises a catalyst comprising platinum (Pt) to sense carbon monoxide (CO) in an environment where both carbon monoxide (CO) and hydrogen ($H_2$) may appear, stabilizing an oxide of platinum ($Pt_xO_y$) of measuring electrode 120 helps reduce or minimize the cross-sensitivity of measuring electrode 120 to hydrogen ($H_2$) because platinum oxide ($Pt_xO_y$) favors carbon monoxide (CO) oxidation while metal platinum (Pt) favors hydrogen ($H_2$) oxidation.

Measuring electrode 120 may comprise any suitable material to help form and/or to help stabilize an oxide of the catalyst in measuring electrode 120.

For one embodiment, measuring electrode 120 may comprise any suitable material having an electrochemical potential more positive than that of the catalyst oxide formation for measuring electrode 120 and less positive than the oxygen evolution reaction at measuring electrode 120. For one embodiment, the mixture of the catalyst with such material helps stabilize measuring electrode 120 at a more positive electrochemical potential relative to an electrode comprising only the catalyst. The higher electrochemical potential for measuring electrode 120 helps shift the equilibrium of the composition of measuring electrode 120 toward catalyst oxide formation, helping to stabilize the amount and composition of the catalyst oxide.

For another embodiment, measuring electrode 120 may comprise any suitable material having an electrochemical potential higher than the oxygen evolution reaction where the oxygen evolution reaction at measuring electrode 120 is kinetically too slow to happen to an observable extend.

The material to help form and/or to help stabilize an oxide of the catalyst of measuring electrode 120 for one embodiment may comprise a suitable reducible metal oxide. The material to help form and/or to help stabilize an oxide of the catalyst of measuring electrode 120 for one embodiment may comprise a suitable reducible transition metal oxide. The material to help form and/or to help stabilize an oxide of the catalyst of measuring electrode 120 for one embodiment may comprise a suitable reducible metal oxide and a suitable oxide of the catalyst material for measuring electrode 120.

Material to help form and stabilize an oxide of the catalyst for one embodiment may comprise a manganese oxide ($Mn_xO_y$), such as manganese dioxide ($MnO_2$). For one embodiment where measuring electrode 120 comprises a catalyst comprising platinum (Pt), manganese dioxide ($MnO_2$) is relatively stable in measuring electrode 120 because the electrochemical potential of platinum oxide ($Pt_xO_y$) formation for PtO is Eo=0.98 volts (V) and for $PtO_2$ is Eo=1.045 V and because the electrochemical potential of the following reaction:

$$MnO_2 + 4H^+ + 2e^- \rightarrow Mn^{2+} + 2H_2O \ (Eo=1.21V)$$

is almost equal to that of the following reaction.

$$O_2 + 4H^+ + 4e^- \rightarrow 2H_2O (Eo=1.23V)$$

The $MnO_2/Mn^{2+}$ reaction neither tends to oxidize oxygen of water ($H_2O$) to elementary oxygen ($O_2$), as higher potential systems do, nor reduces dissolved oxygen ($O_2$) to water ($H_2O$), as lower potential systems do.

For another embodiment where measuring electrode 120 comprises a catalyst comprising platinum (Pt), measuring electrode 120 may comprise a manganese oxide ($Mn_xO_y$), such as manganese dioxide ($MnO_2$), and a platinum oxide ($Pt_xO_y$), such as platinum dioxide ($PtO_2$), to help form and stabilize an oxide of the catalyst.

The material to help form and/or to help stabilize an oxide of the catalyst of measuring electrode 120 for another embodiment may comprise a ruthenium oxide ($Ru_xO_y$), such as ruthenium dioxide ($RuO_2$). For one embodiment where measuring electrode 120 comprises a catalyst comprising platinum (Pt), ruthenium dioxide ($RuO_2$) is relatively stable in measuring electrode 120 because the electrochemical potential for the reaction $RuO_2/Ru^{2+}$ is Eo=1.12 V.

The material to help form and/or to help stabilize an oxide of the catalyst of measuring electrode 120 for another embodiment may comprise an osmium oxide ($Os_xO_y$), such as osmic tetroxide ($OsO_4$). For one embodiment where measuring electrode 120 comprises a catalyst comprising platinum (Pt), osmic tetroxide ($OsO_4$) is relatively stable in measuring electrode 120 because the electrochemical potential for the reaction $OsO_4/OsO_2$ is Eo=1.02 V.

Although described in connection with a catalyst comprising platinum (Pt) for measuring electrode 120, the addition of material to a catalyst for measuring electrode 120 to help form and/or to help stabilize an oxide of the catalyst may possibly be extended to other suitable catalyst materials including, for example, a suitable platinum group metal or a suitable noble metal including silver (Ag) and gold (Au).

For block 206, sensor operating circuitry 105 measures current flow between measuring electrode 120 and sensor operating circuitry 105. Sensor operating circuitry 105 may comprise any suitable circuitry to measure such current in any suitable manner.

For block 208, sensor operating circuitry 105 identifies whether a target particle is near sensor cell 102 based on the measured current. Sensor operating circuitry 105 may identify whether a target particle is near sensor cell 102 in any suitable manner based on the measured current.

Sensor operating circuitry 105 for one embodiment may compare the measured current to a predetermined value to identify whether a target particle is near sensor cell 102 based on the relationship between the measured current and the predetermined value. Sensor operating circuitry 105 for one embodiment may identify an amount or concentration of a target particle near sensor cell 102 based on the measured current, noting for one embodiment that the production of electrons resulting from an oxidation reaction at measuring electrode 120 is generally proportional to the amount or concentration of a target particle near sensor cell 102.

Because stabilizing an oxide of the catalyst of measuring electrode 120 for one embodiment helps prevent the oxidation of potentially interfering non-target particles and therefore helps prevent inducing current between measuring electrode 120 and sensor operating circuitry 105 due to the presence of such non-target particles, sensor operating circuitry 105 may identify a presence and/or an amount or concentration of a target particle in an environment in which such non-target particles may appear with relatively more accuracy.

If sensor operating circuitry 105 identifies for block 208 that a target particle is near sensor cell 102, sensor operating circuitry 105 for one embodiment for block 210 may output a signal indicating the presence of a target particle to output device 180. Sensor operating circuitry 105 for one embodiment may output a signal indicating the amount or concentration of a target particle sensed with sensor cell 102. If sensor operating circuitry 105 identifies for block 208 that a target particle is not near sensor cell 102, sensor operating circuitry 105 for one embodiment for block 212 may output a signal indicating the absence of a target particle to output device 180.

Output device 180 may comprise any suitable circuitry and/or equipment to respond to a signal output from sensor operating circuitry 105 in any suitable manner. Output device 180 for one embodiment may provide a suitable auditory output and/or a suitable visual output in response to a signal from sensor operating circuitry 105. Output device 180 for one embodiment may provide a suitable auditory output and/or a suitable visual output to indicate the amount or concentration of a target particle sensed with sensor cell 102. Output device 180 for one embodiment may provide a suitable tactile output, such as vibration for example, in response to a signal from sensor operating circuitry 105. Output device 180 for one embodiment may actuate other circuitry and/or equipment in response to a signal from sensor operating circuitry 105, for example, to help control a process involving a target particle or to help clear a target particle from an environment near sensor cell 102.

Sensor operating circuitry 105 for one embodiment may repeat operations for blocks 204, 206, 208, 210, and/or 212 to continue to bias one or more electrodes of sensor 100 to a suitable electrical potential and monitor current flow between measuring electrode 120 and sensor operating circuitry 105.

Sensor operating circuitry 105 may perform operations for blocks 204-212 in any suitable order and may or may not overlap in time the performance of any suitable operation with any other suitable operation. Sensor operating circuitry 105 for one embodiment may, for example, perform operations for blocks 204, 206, 208, 210, and/or 212 substantially continuously or discretely at a suitable rate.

Sensor operating circuitry 105 for another embodiment may output a signal to output device 180 for block 210 generally only when the absence of a target particle was identified based on a just prior current measurement and/or when an identified amount or concentration of a target particle near sensor cell 102 changes, or changes beyond a certain amount, from a prior sensing. Sensor operating circuitry 105 for another embodiment may output a signal to output device 180 for block 212 generally only when the presence of a target particle was identified based on a just prior current measurement.

Sensor Formation

Figure 3:
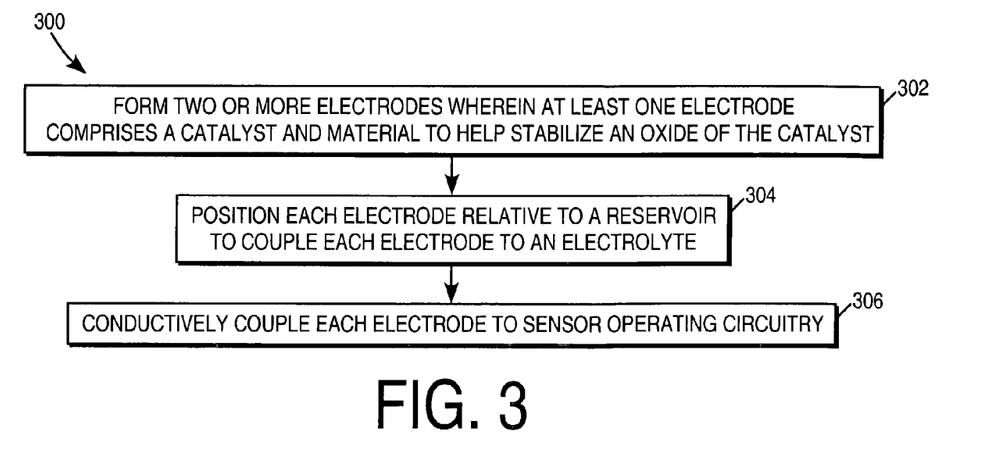
FIG. 3 illustrates, for one embodiment, a flow diagram to form an electrochemical sensor having an electrode comprising a catalyst and material to help stabilize an oxide of the catalyst.

FIG. 3 illustrates, for one embodiment, a flow diagram 300 to form sensor 100.

For block 302 of FIG. 3, two or more electrodes are formed. Such electrodes may be formed in any suitable manner. For one embodiment, at least one electrode is formed to comprise a catalyst and material to help stabilize an oxide of the catalyst.

Measuring electrode 120 may be formed in any suitable manner from any suitable material.

Measuring electrode 120 for one embodiment may be formed by mixing a catalyst powder with powder for material to help form and/or to help stabilize an oxide of the catalyst. For one embodiment, the powder mixture may also be mixed with a powder or emulsion of a suitable binder material, such as polytetrafluoroethylene (PTFE) for example, to produce an emulsion that may be spread onto a suitable porous substrate for mechanical strength. The substrate for one embodiment may also serve as a diffusion barrier. The resulting emulsion for one embodiment may be spread onto membrane 124. The substrate for one embodiment may then be subjected to a suitable heat treatment to help bond the emulsion to the substrate and remove solvents.

Measuring electrode 120 for one embodiment may comprise a catalyst comprising platinum (Pt) and comprise manganese dioxide ($MnO_2$) to help form and stabilize a platinum oxide ($Pt_xO_y$) in measuring electrode 120. Measuring electrode 120 for one embodiment may be formed from any suitable powder mixture having any suitable amount of platinum black (Pt) and manganese dioxide ($MnO_2$) powder. A higher manganese dioxide ($MnO_2$) content may decrease the conductivity of measuring electrode 120 and decrease the total amount of platinum black (Pt) per square area, thereby decreasing sensitivity to a target particle and/or increasing the response time. A lower manganese dioxide ($MnO_2$) content may not provide for sufficient contact of platinum black (Pt) particles with the oxidant particles, thereby increasing sensitivity to non-target particles. A lower manganese dioxide ($MnO_2$) content may also potentially decrease the duration of low cross-sensitivity to non-target particles.

The mass mixing ratio of platinum black (Pt) to manganese dioxide ($MnO_2$) for one embodiment is in the range of approximately 100:1 to approximately 3:1.

The mass mixing ratio of platinum black (Pt) to manganese dioxide ($MnO_2$) for one embodiment is in the range of approximately 10:1 to approximately 5:1.

Measuring electrode 120 for one embodiment may comprise approximately 11 $mg/cm^2$ platinum black (Pt) and approximately 2 $mg/cm^2$ manganese dioxide ($MnO_2$) for a mass mixing ratio of approximately 5.5:1.

Measuring electrode 120 for one embodiment may be formed from only platinum black (Pt) and manganese dioxide ($MnO_2$).

Measuring electrode 120 for one embodiment may comprise a catalyst comprising platinum (Pt) and comprise both a platinum oxide ($Pt_xO_y$), such as platinum dioxide ($PtO_2$), and manganese dioxide ($MnO_2$) to help form and stabilize a platinum oxide ($Pt_xO_y$) in measuring electrode 120. Measuring electrode 120 for one embodiment may be formed from any suitable powder mixture having any suitable amount of platinum black (Pt), a platinum oxide ($Pt_xO_y$) powder, and manganese dioxide ($MnO_2$) powder.

For one embodiment, the powder mixture for measuring electrode 120 may comprise less than approximately 20% of a platinum oxide ($Pt_xO_y$) powder and less than approximately 30% of manganese dioxide ($MnO_2$) powder of the total weight of the powder mixture.

For one embodiment, the powder mixture for measuring electrode 120 may comprise in the range of approximately 5% to approximately 15% of a platinum oxide ($Pt_xO_y$) powder and in the range of approximately 5% to approximately 20% of manganese dioxide ($MnO_2$) powder of the total weight of the powder mixture.

For one embodiment, the powder mixture for measuring electrode 120 may comprise approximately 10% of a platinum oxide ($Pt_xO_y$) powder and approximately 10% manganese dioxide ($MnO_2$) powder of the total weight of the powder mixture.

Measuring electrode 120 for one embodiment may be formed from only platinum black (Pt), a platinum oxide ($Pt_xO_y$), and manganese dioxide ($MnO_2$).

As measuring electrode 120 comprising either $Pt/MnO_2$ or $Pt/PtO_2/MnO_2$ is produced in ambient air, surface oxides form on measuring electrode 120 in a manner that may depend, for example, on the pH of electrolyte 150 and on the electrochemical potential of measuring electrode 120. Surface oxides may form independent from any added platinum dioxide ($PtO_2$). The structure of the surface oxides is not known but is suspected to consist of stoichiometrically non-defined thin platinum oxide ($Pt_xO_y$) clusters or films of different size and shape. Manganese dioxide ($MnO_2$) and/or platinum dioxide ($PtO_2$) are thought to help stabilize these surface oxides.

Reference electrode 130 may be formed in any suitable manner from any suitable material. Reference electrode 130 for one embodiment may be formed similarly as measuring electrode 120 to help prevent any non-target particles that leak to reference electrode 130 from shifting the electrical potential of reference electrode 130 to produce a negative zero current.

Reference electrode 130 for one embodiment may be formed by mixing a suitable powder or powder mixture for reference electrode 130 with a powder or emulsion of a suitable binder material, such as polytetrafluoroethylene (PTFE) for example, to produce an emulsion that may be spread onto a suitable porous substrate 134 for mechanical strength. Substrate 134 for one embodiment may also serve as a diffusion barrier. Substrate 134 for one embodiment may then be subjected to a suitable heat treatment to help bond the emulsion to the substrate and remove solvents. Substrate 134 may be formed from any suitable material, such as polytetrafluoroethylene (PTFE) for example.

Counter electrode 140 may be formed in any suitable manner from any suitable material that may depend, for example, on the reaction to be catalyzed by counter electrode 140. Where counter electrode 140 is to reduce oxygen ($O_2$), for example, counter electrode 140 may be formed to comprise gold (Au), silver (Ag), or platinum (Pt), for example.

Counter electrode 140 for one embodiment may be formed by mixing a suitable powder or powder mixture for counter electrode with a powder or emulsion of a suitable binder material, such as polytetrafluoroethylene (PTFE) for example, to produce an emulsion that may be spread onto a suitable porous substrate 144 for mechanical strength. Substrate 144 for one embodiment may also serve as a diffusion barrier. Substrate 144 for one embodiment may then be subjected to a suitable heat treatment to help bond the emulsion to the substrate and remove solvents. Substrate 144 may be formed from any suitable material, such as polytetrafluoroethylene (PTFE) for example.

For block 304 of FIG. 3, each electrode is positioned relative to a reservoir to couple each electrode to electrolyte 150. Each electrode may be positioned in any suitable manner relative to a reservoir to hold electrolyte 150. For one embodiment, as illustrated in FIG. 1, housing 110 supports measuring electrode 120, reference electrode 130, and counter electrode 140 in the reservoir containing electrolyte 150.

Electrolyte 150 may comprise any suitable solution. For one embodiment, electrolyte 150 may be a hydrophilic electrolyte, such as a solution of sulfuric acid in water for example. Hydrophilic separators or wetting filters may also be positioned relative to one or more electrodes and electrolyte 150 to aid ionic electrical contact between electrodes.

For block 306 of FIG. 3, each electrode is conductively coupled to sensor operating circuitry 105. Each electrode may be conductively coupled to sensor operating circuitry 105 in any suitable manner.

In the foregoing description, one or more embodiments of the present invention have been described. It will, however, be evident that various modifications and changes may be made thereto without departing from the broader spirit or scope of the present invention as defined in the appended claims. The specification and drawings are, accordingly, to be regarded in an illustrative rather than a restrictive sense.

What is claimed is:

1. A carbon monoxide sensor cell comprising:
a compartment comprising at least one opening for introduction of a sensing gas;
an electrolyte comprising a hydrophilic acid contained in the compartment; and
at least one electrode positioned in the compartment and in contact with the electrolyte, said electrode comprising a metal catalyst, an oxide of the metal catalyst and a transition metal oxide material to help stabilize the oxide of the metal catalysts,
wherein the hydrophilic acid in said electrolyte is adapted to enable CO sensing by said sensor cell.

2. The sensor cell of claim 1, wherein the material helps form the oxide of the catalyst.

3. The sensor cell of claim 1, wherein the catalyst comprises platinum.

4. The carbon monoxide sensor cell of claim 1, wherein the electrolyte comprises an aqueous solution of sulfuric acid.

5. A sensor cell comprising:
a compartment comprising at least one opening for introduction of a sensing gas;
an electrolyte comprising a hydrophilic acid contained in the compartment; and
at least one electrode positioned in the compartment and in contact with the electrolyte, said electrode comprising a metal catalyst, an oxide of the metal catalyst metal and a transition metal oxide material to help stabilize the oxide of the metal catalyst, wherein the catalyst comprises platinum and the material to help stabilize an oxide of the catalyst comprises manganese dioxide; and wherein the mass mixing ratio of platinum to manganese dioxide is in the range of approximately 100:1 to approximately 3:1.

6. The sensor cell of claim 5, wherein the mass mixing ratio of platinum to manganese dioxide is in the range of approximately 10:1 to approximately 5:1.

7. A sensor cell comprising an electrolyte and an electrode that comprises a catalyst and material to help stabilize an oxide of the catalyst, wherein the catalyst comprises platinum and the material to help stabilize an oxide of the catalyst comprises a mixture containing both a platinum oxide and manganese dioxide; and wherein the electrode is formed from a powder mixture comprising less than approximately 20% of a platinum oxide powder and less than approximately 30% of manganese dioxide powder of the total weight of the powder mixture.

8. A sensor cell comprising an electrolyte and an electrode that comprises a catalyst and material to help stabilize an oxide of the catalyst, wherein the catalyst comprises platinum and the material to help stabilize an oxide of the catalyst comprises a mixture containing both a platinum oxide and manganese dioxide; and wherein the electrode is formed from a powder mixture comprising in the range of approximately 5% to approximately 15% of a platinum oxide powder and in the range of approximately 5% to approximately 20% of manganese dioxide powder of the total weight of the powder mixture.

9. An electrode comprising a catalyst, manganese dioxide and a platinum oxide, wherein the electrode is formed from a powder mixture comprising less than approximately 20% of a platinum oxide powder and less than approximately 30% of manganese dioxide powder of the total weight of the powder mixture.

10. An electrode comprising a catalyst, manganese dioxide and a platinum oxide, wherein the electrode is formed from a powder mixture comprising in the range of approximately 5% to approximately 15% of a platinum oxide powder and in the range of approximately 5% to approximately 20% of manganese dioxide powder of the total weight of the powder mixture.

11. A carbon monoxide electrochemical sensor comprising:
a compartment comprising at least one opening for introduction of a sensing gas;
a measuring electrode comprising a metal catalyst, an oxide of the metal catalyst and a transition metal oxide material to help stabilize the oxide of the metal catalyst;
a counter electrode;
an electrolyte in contact with the measuring and counter electrodes, said electrolyte comprising a hydrophilic acid, wherein the measuring electrode, counter electrode and electrolyte are positioned within the compartment; and
sensor operating circuitry coupled to the measuring electrode and counter electrodes,
wherein the hydrophilic acid in said electrolyte is adapted to enable CO sensing by said sensor cell, and
wherein the metal catalyst comprises a platinum component and the transition metal oxide material to help stabilize the oxide of the metal catalyst comprises manganese dioxide; and wherein the mass mixing ratio of the platinum component to manganese dioxide is in the range of approximately 100:1 to approximately 1:1.

12. The sensor of claim 11, wherein the material helps form the oxide of the catalyst.

13. The sensor of claim 11, wherein the catalyst of the measuring electrode comprises platinum.

14. The sensor of claim 11, comprising a reference electrode comprising a catalyst and material to help stabilize an oxide of the catalyst of the reference electrode.

15. A method for forming a carbon monoxide sensor cell, comprising:
fabricating a reservoir having at least one inlet for introduction of the sensing gas;
forming two or more electrodes, wherein at least one electrode comprises a metal catalyst, an oxide of the metal catalyst and a transition metal oxide material to help stabilize the oxide of the metal catalyst; and
positioning the two or more electrodes relative to a reservoir to couple the two or more electrodes to an electrolyte in the reservoir, wherein said electrolyte comprises a hydrophilic acid that is adapted to enable CO sensing by said sensor cell.

16. The method of claim 15, wherein the forming comprises fanning the at least one electrode to comprise material that helps form the oxide of the catalyst.

17. The method of claim 15, wherein the forming comprises forming the at least one electrode to comprise a metal oxide to help stabilize an oxide of the catalyst.

18. The method of claim 15, comprising coupling sensor operating circuitry to the two or more electrodes.

19. The method of claim 15, wherein the electrolyte comprises an aqueous solution of sulfuric acid.

20. A method for determining presence of a carbon monoxide target particle, comprising:
providing a compartment with an inlet entry for introduction of a gas suspected of including the target particle;
introducing a gas biasing one or more electrodes coupled to an electrolyte that comprises a hydrophilic acid that is adapted to enable CO sensing, wherein at least one electrode comprises a metal catalyst, an oxide of the metal catalyst and a transition metal oxide material to help stabilize the oxide of the metal catalyst;

measuring any current produced from one of the electrodes; and identifying whether the carbon monoxide target particle is present based on the measured current.

21. The method of claim 20, wherein the at least one electrode comprises platinum as the catalyst.

22. The method of claim 20, wherein the electrolyte comprises an aqueous solution of sulfuric acid.

23. A sensor cell comprising a compartment with at least one opening to ambient surroundings, an aqueous electrolyte and at least one electrode positioned within the compartment, wherein one electrode comprises a metal catalyst and material to help stabilize an oxide of the metal catalyst, wherein the material to help stabilize an oxide of the metal catalyst comprises a mixture containing both a platinum oxide and manganese dioxide.

24. The sensor cell of claim 23, wherein the catalyst comprises platinum.

25. A method for forming a sensor cell, comprising:

forming a compartment cell having at least one inlet for introduction of the sensing gas;

forming two or more electrodes, wherein at least one electrode comprises a metal catalyst, manganese dioxide, and a platinum oxide; and positioning the two or more electrodes relative to a reservoir to couple the two or more electrodes to an aqueous electrolyte in the reservoir.

26. The method of claim 25, wherein the catalyst comprises platinum.

27. A method for determining presence of a target particle, comprising:

providing a compartment with an inlet entry for introduction of a gas suspected of including the target particle;

biasing one or more electrodes in contact with an aqueous electrolyte, wherein at least one electrode comprises a metal catalyst, manganese dioxide, and a platinum oxide;

measuring any current produced from one of the electrodes; and identifying whether the target particle is present based on the measured current.

28. The method of claim 27, wherein the metal catalyst comprises platinum.

* * * * *

UNITED STATES PATENT AND TRADEMARK OFFICE
CERTIFICATE OF CORRECTION

PATENT NO. : 7,156,968 B2
APPLICATION NO. : 10/435618
DATED : January 2, 2007
INVENTOR(S) : Serguei Tsapakh et al.

It is certified that error appears in the above-identified patent and that said Letters Patent is hereby corrected as shown below:

In column 11, line 13 (claim 1), "catalysts" should be -- catalyst --.

In column 12, line 22 (claim 11), "electrodes" should be -- electrode --.

In column 12, line 52 (claim 16), "fanning" should be -- forming --.

Signed and Sealed this

Twenty-seventh Day of March, 2007

JON W. DUDAS
*Director of the United States Patent and Trademark Office*